United States Patent
Clayton et al.

(10) Patent No.: US 8,377,939 B2
(45) Date of Patent: *Feb. 19, 2013

(54) OXADIAZOLE DERIVATIVES AND THEIR USE AS METABOTROPIC GLUTAMATE RECEPTOR POTENTIATORS 842

(75) Inventors: Joshua Clayton, Oakville (CA); Ian Egle, North York (CA); James Empfield, Wilmington, DE (US); James Folmer, Wilmington, DE (US); Methvin Isaac, Brampton (CA); Fupeng Ma, Melrose, MA (US); Abdelmalik Slassi, Mississauga (CA)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/134,553

(22) Filed: Jun. 6, 2008

(65) Prior Publication Data
US 2008/0306077 A1 Dec. 11, 2008

Related U.S. Application Data

(60) Provisional application No. 60/942,553, filed on Jun. 7, 2007.

(51) Int. Cl.
*A61K 31/496* (2006.01)
*C07D 413/04* (2006.01)
(52) U.S. Cl. .................... 514/254.03; 544/367
(58) Field of Classification Search .......... None
See application file for complete search history.

(56) References Cited

U.S. PATENT DOCUMENTS

| | | | |
|---|---|---|---|
| 3,993,617 | A | 11/1976 | Schwan |
| 5,175,157 | A | 12/1992 | Psiorz |
| 5,681,954 | A | 10/1997 | Yamamoto et al. |
| 6,017,919 | A | 1/2000 | Inaba et al. |
| 7,799,792 | B2 | 9/2010 | Clayton et al. |
| 2003/0212094 | A1 | 11/2003 | Yamabe |
| 2005/0026976 | A1 | 2/2005 | Curtin et al. |
| 2008/0227794 | A1 | 9/2008 | Van Wagenen et al. |
| 2008/0306077 | A1 | 12/2008 | Clayton et al. |
| 2008/0306088 | A1 | 12/2008 | Clayton et al. |
| 2009/0111830 | A1 | 4/2009 | Wagenen et al. |
| 2009/0149505 | A1 | 6/2009 | Empfield et al. |
| 2009/0275578 | A1 | 11/2009 | Clayton et al. |

FOREIGN PATENT DOCUMENTS

| | | |
|---|---|---|
| EP | 1528923 | 10/1978 |
| EP | 0548934 | 6/1993 |
| EP | 0602814 | 6/1994 |
| EP | 1431267 | 6/2004 |
| EP | 1726585 | 11/2006 |
| WO | 9217448 | 4/1991 |
| WO | 9854135 | 12/1998 |
| WO | 9926927 | 6/1999 |
| WO | 0210146 | 2/2002 |
| WO | 03101450 | 1/2003 |
| WO | 03087044 | 10/2003 |
| WO | 2004024702 | 3/2004 |
| WO | 2004031178 | 4/2004 |
| WO | 2004087048 | 10/2004 |
| WO | 2004089897 | 10/2004 |
| WO | 2005040157 | 5/2005 |
| WO | 2005074643 | 8/2005 |
| WO | 2005080397 | 9/2005 |
| WO | 2005085214 | 9/2005 |
| WO | 2005085216 | 9/2005 |
| WO | 2005100351 | 10/2005 |
| WO | 2006020879 | 2/2006 |
| WO | 2006047237 | 5/2006 |
| WO | 2006091496 | 8/2006 |
| WO | 2006123249 | 11/2006 |
| WO | 2006123255 | 11/2006 |
| WO | 2007000339 | 1/2007 |
| WO | 2007021308 | 2/2007 |
| WO | 2007021309 | 2/2007 |
| WO | 2007039439 | 4/2007 |
| WO | 2007095024 | 8/2007 |

OTHER PUBLICATIONS

Vippagunta et al. Advanced Drug Delivery Reviews, vol. 48, pp. 3-26 (2001).*
Eduardo E. Benarroch; "Metabotropic glutamate receptors: Synaptic modulators and therapeutic targets for neurologic disease"; Neurology 2008;70; pp. 964-968.
Sandeep T. Patil, et al.; Activation of mGLu2/3 receptors as a new approach to treat schizophrenia: a randomized Phase 2 clinical trial; Nature Medicine vol. 13, No. 9, Sep. 2007; pp. 1102-1107.
Orito Kazuhiko, et al; "Preparation of benzolactams by Pd(OAc)2-catalyzed direct aromatic carbonylation"; Journal of the American Chemical Society; Nov. 10, 2004; vol. 126, No. 44; pp. 14342-14343; ISSN: 0002-7863, Table 2, Compound 10B.
Tsuritani T, et al; "A short and efficient synthesis of isoindolin-1-ones", Synlett, Mar. 17, 2006, Germany, No. 5, pp. 801-803, ISSN: 0936-5214, Table 2, Compound 7. Couture, A., et al, "Diastereoselective Addition of Metalated Isoindolin-1-ones . . . (E)-3-Arylideneisoindolin-1-Ones", Tetrahedron Letters, vol. 43, No. 12, Mar. 18, 2002, pp. 2207-2210 XP004344002.
Casagrande, C., et al, "Synthesis of Some Isoindolines . . . Neuron Blocking Agents", IL Farmaco, Edizione Scientifica, vol. 27, No. 6, Jun. 1972, pp. 445-470 XP000571647.

(Continued)

*Primary Examiner* — Emily Bernhardt
(74) *Attorney, Agent, or Firm* — Kenneth F. Mitchell

(57) ABSTRACT

Compounds of Formula I:

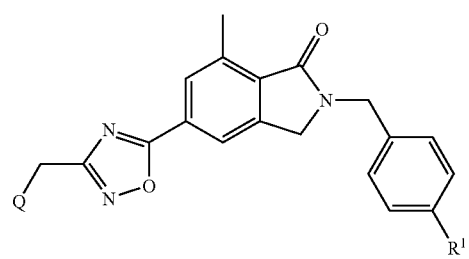

wherein $R^1$ and Q are as described in the specification, pharmaceutically-acceptable salts, methods of making, pharmaceutical compositions containing and methods for using the same.

4 Claims, No Drawings

OTHER PUBLICATIONS

Morissette, et al. "High-throughput crystallization: polymorphs, salts, co-crystals and solvates of pharmaceutical solids". Advanced Drug Delivery Reviews 2004, 56, pp. 275-300.

Souillac, et al., "Characterization of Delivery systems, Differential Scanning Calorimetry", pp. 217-218 (in Encyclopedia of Controlled Drug Delivery, 1999, John Wiley & Sons, pp. 212-227).

Yamamoto, et al., "Synthesis of benzo-fused lactams . . . conjugated carbonyl groups", Org Biomol. Chem (2004); vol. 2, 1287-1294.

Moreau, et al, "A new approach to isoindoloisoquinolinones. A simple synthesis of neuvamine", Tetrahedron, vol. 60, No. 29, Jul. 12, 2004, pp. 6169-6176.

Anderson, et al., "Synthesis of 9,10-dihydroanthracen-9,10-imines", Journal of Organic Chemistry, vol. 44, No. 9, 1979, pp. 1519-1515.

Luzzio, et al, "A facile scheme for phthalimide—phthalimidine conversion", Tetrahedron Letters, vol. 40, No. 11, Mar. 12, 1999, pp. 2087-2090.

Hatt, et al, "Heterocyclic nitrogen compounds . . . in a Clemmensen reductionth", Journal of the Chemical Society, 1952, pp. 199-205.

Clayden, Jonathan., et al, "Dearomatizing Anionic Cyclization of Substituted N-Cumyl-N-Benzyl-Benzamides . . . Substituted Isoindolones", Organic Letters, vol. 2, No. 26, 2000, pp. 4229-4232 XP002345295.

Bailey, et al., "2,3-Diarylphthalimidines", Journal of Medicinal Chemistry, vol. 14, No. 3, pp. 240-241.

Mori, et al, "Reactions and syntheses with organometallic compounds. 7. Synthesis of benzolactams by palladium-catalyzed amidation", Journal of Organic Chemistry, vol. 43, No. 9, Apr. 28, 1978, pp. 1684-1687.

Grigg, et al, "Isoindolinones via a room temperature . . . carbonylation-amination cascade", Tetrahedron Letters, vol. 44, No. 37, Sep. 8, 2003, pp. 6979-6982.

Norman, et al, "Effect of linking bridge modifications on the antipsychotic profile of some phthalimide and isoindolinone derivatives", Journal of Medicinal Chemistry, vol. 39, No. 1, 1996, pp. 149-157.

Zhuang, et al, "Isoindol-1-one analogues . . . receptor ligands", Journal of Medicinal Chemistry, vol. 41, No. 2, Jan. 15, 1998, pp. 157-166.

Norman, et al, "Conformationally restricted analogues of remoxipride as potential antipsychotic agents" Journal of Medicinal Chemistry, vol. 36, No. 22, Oct. 29, 1993, pp. 3417-3423.

Ahn, et al, "N-Substituted-3-arylpyrrolidines: potent and selective ligands at serotonin 1A receptor", Bioorganic & Medicinal Chemistry Letters, vol. 9, No. 10, May 17, 1999, pp. 1379-1384.

Sugimoto, et al, "Synthesis and structure-activity . . . and related derivatives" Journal of Medicinal Chemistry, vol. 35, No. 24, 1992, pp. 4542-4548.

Mayer, et al, "New substituted . . . antagonist activity", Journal of Medicinal Chemistry, vol. 43, Sep. 19, 2000, pp. 3653-3664.

Breytenbach, et al, "Synthesis and antimicrobial activity of some isoindolin-1-ones derivatives", Bioorganic & Medicinal Chemistry Letters, vol. 10, No. 15, Aug. 7, 2000, pp. 1629-1631.

Hidemi Yoda, et al., "A New Entry for the Preparation of Substituted Aromatic . . . by Samarium(II) Iodide", Synthetic Communications 33(7), 1087-1094, 2003.

Chan Sik Cho, et al., "Synthesis of Isoindolin-1- . . . Chloride and Imines", Tetrahedron Letters, 41(2000), pp. 3891-3893.

Terao, et al., "Alkylation of Phthalimidines", Chemical & Pharmaceutical Bulletin, vol. 23(1), pp. 184-187, 1975, CA 83:9678.

Fabrycy, et al., "Pochodne Izoindoliny . . . 3-Dwumetyloftalimidyn", Roczniki Chemii, 47(5), pp. 937-942, 1973, CA 79:105030.

Bonnefous, et al., "Biphenyl-Indanones: Allosteric Potentiators . . . Subtype 2 Receptor", Bioorganic & Medicinal Chemistry Letters, vol. 15. pp. 4354-4358 (2005).

Bonnefous, et al. (Merck), poster presented at the 229th National Meeting of the American Chemical Society, San Diego, CA, Mar. 2005; Poster MEDI-37.

Eric Mertz, et al, "Synthetic Receptors for CG Base Pairs", Organic Letters, 2000, vol. 2, No. 19, pp. 2931-2934.

Hyoung-Gon Lee, et al, "The Role of Metabotropic Glutamate Receptors in Alzheimer's Disease", Acta Neurobiol Exp 2004, 64(1): pp. 89-98.

Barr, et al., "Palladium-Assisted Organic Reactions . . . 3-Disubstituted Phthalimidines", Journal of Organometallic Chemistry, vol. 302, No. 1, Mar. 11, 1986, pp. 117-126, XP002383544.

Hoarau C, et al, "A Versatile Synthesis of Poly- and Diversely Substituted Isoindolin-1-ones", Synthesis No. 5, 2000, pp. 655-660, XP002383545.

Rys, V, et al, "A Short Total Synthesis of the Alkaloids Piperolactam C, Goniopedaline, and Stigmalactam", European Journal of Organic Chemistry, No. 7, Apr. 2003, pp. 1231-1237, XP002383546.

* cited by examiner

OXADIAZOLE DERIVATIVES AND THEIR USE AS METABOTROPIC GLUTAMATE RECEPTOR POTENTIATORS 842

BACKGROUND

The present invention relates to novel compounds that function as potentiators of glutamate receptors, methods for their preparation, pharmaceutical compositions containing them and their use in therapy.

The metabotropic glutamate receptors (mGluR) constitute a family of GTP-binding-protein (G-protein) coupled receptors that are activated by glutamate, and have important roles in synaptic activity in the central nervous system, including neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolini, 1999, Prog. Neurobiol. 59:55).

Eight mGluR subtypes have been identified, which are divided into three groups based upon primary sequence similarity, signal transduction linkages, and pharmacological profile. Group-I includes mGluR1 and mGluR5, which activate phospholipase C and the generation of an intracellular calcium signal. The Group-II (mGluR2 and mGluR3) and Group-III (mGluR4, mGluR6, mGluR7, and mGluR8) mGluRs mediate an inhibition of adenylyl cyclase activity and cyclic AMP levels. For a review, see Pin et al., 1999, Eur. J. Pharmacol., 375:277-294.

Activity of mGluR family receptors are implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365; Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, supra; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

DESCRIPTION OF THE INVENTION

We have identified a class of compounds that modulate mGluR function. In one aspect the invention provides compounds of Formula I, or a pharmaceutically acceptable salt, hydrate, solvate, optical isomer, or combination thereof:

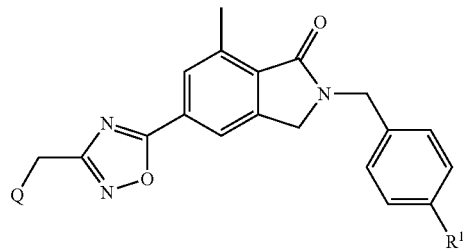

Formula I wherein
$R^1$ is halo or $C_{1-3}$haloalkoxyl;
Q is

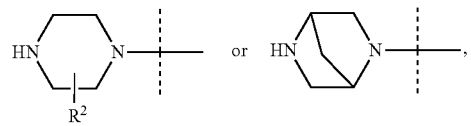

and $R^2$ is hydrogen or $C_{1-3}$alkyl, or a pharmaceutically acceptable salt, hydrate, solvate, optical isomer, or combination thereof.

The invention also provides processes for the preparation of compounds of Formula I.

The invention further provides a pharmaceutical composition comprising a compound according to Formula I together with a pharmaceutically acceptable carrier or excipient; in another aspect, the invention provides a method for the treatment or prevention of neurological and psychiatric disorders associated with glutamate dysfunction in an animal in need of such treatment. The method comprises the step of administering to the animal a therapeutically effective amount of a compound of Formula I or a pharmaceutical composition comprising such an amount.

The invention also provides for the use of a compound according to Formula I or a pharmaceutically acceptable salt or solvate thereof, in the manufacture of a medicament for the treatment of conditions mentioned herein.

Further, the invention provides a compound of Formula I, or a pharmaceutically acceptable salt or solvate thereof, for use in therapy.

Compounds described herein exhibit activity as modulators of metabotropic glutamate receptors and more particularly exhibit activity as potentiators of the mGluR2 receptor. It is contemplated that the compounds will be useful in therapy as pharmaceuticals, in particular, for the treatment of neurological and psychiatric disorders associated with glutamate dysfunction.

DEFINITIONS

Unless described otherwise within this specification, the nomenclature used in this specification generally follows the examples and rules stated in *Nomenclature of Organic Chemistry*, Sections A, B, C, D, E, F and H, Pergamon Press, Oxford, 1979, which is incorporated by references herein for its exemplary chemical structure names and rules on naming chemical structures. Optionally, a name of a compound may be generated using a chemical naming program: ACD/Chem-Sketch, Version 5.09/September 2001, Advanced Chemistry Development, Inc., Toronto, Canada.

The term "$C_{1-3}$alkyl" as used herein means a straight-, branched-chain or cyclic hydrocarbon radical having from one to three carbon atoms, and includes methyl, ethyl, propyl, isopropyl, and cyclopropyl.

The term "$C_{1-3}$haloalkoxyl" as used herein means a straight- or branched-chain alkoxy radical having from one to three carbon atoms and at least one halo substituent and includes fluoromethoxyl, trifluoromethoxyl, fluoroethoxyl, trifluoropropyloxyl, fluoroisopropyloxy and the like.

The term "halo" as used herein means halogen and includes fluoro, chloro, bromo, iodo, in both radioactive and non-radioactive forms.

The symbol Δ when used herein means heating or the application of heat.

The term "pharmaceutically acceptable salt" means either an acidic addition salt or a basic addition salt that is compatible with the administration to patients.

A "pharmaceutically acceptable acidic addition salt" is any non-toxic organic or inorganic acidic addition salt of a compound represented by Formula I. Illustrative inorganic acids that form suitable salts include hydrochloric, hydrobromic, sulfuric and phosphoric acid and acid metal salts such as sodium monohydrogen orthophosphate and potassium hydrogen sulfate. Illustrative organic acids that form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Where chemically feasible, mono- or di-acid salts can be formed and such salts can exist in either a hydrated solvated or substantially anhydrous form. In general, the acidic addition salts of these compounds are more soluble in water and various hydrophilic organic solvents and generally demonstrate higher melting points in comparison to their free base forms. Other non-pharmaceutically acceptable salts, e.g. oxalates, may be used, for example in the isolation of compounds of Formula I for laboratory use or for subsequent conversion to a pharmaceutically acceptable acidic addition salt.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis or to prevent or slow the appearance of symptoms of the named disorder or condition.

The term "therapeutically effective amount" means an amount of the compound that is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds

The described compounds conform generally to Formula I:

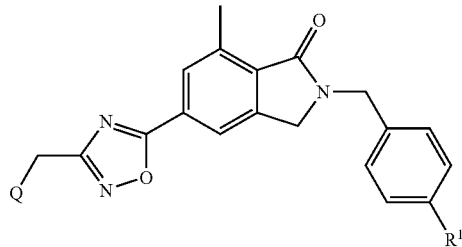

Formula I wherein
$R^1$ is halo or $C_{1-3}$haloalkoxyl;
Q is

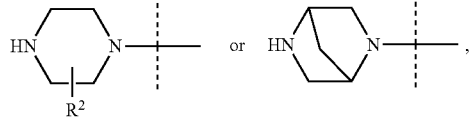

and
$R^2$ is hydrogen or $C_{1-3}$alkyl, or a pharmaceutically acceptable salt, hydrate, solvate, optical isomer, or combination thereof.

In a particular embodiment $R^1$ is chloro or trifluoromethoxyl.

In another embodiment $R^1$ is trifluoromethoxyl.

In yet another embodiment Q is

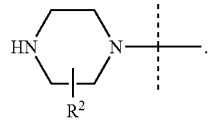

In still yet another embodiment Q is

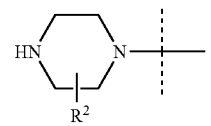

where $R^2$ is H.

In a further embodiment, $R^1$ is chloro or trifluoromethoxyl, Q is

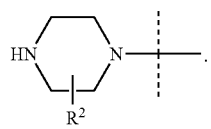

In yet a further embodiment $R^1$ is trifluoromethoxyl and Q is

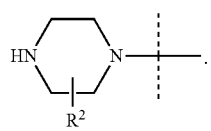

In still a further embodiment $R^1$ is chloro or trifluoromethoxyl and Q is

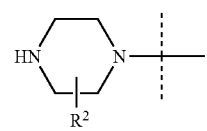

wherein $R^2$ is H.

In another embodiment $R^1$ is chloro or trifluoromethoxyl and Q is

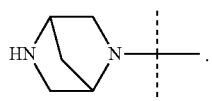

A pharmaceutically acceptable salt, hydrate, solvate, optical isomer, or combination thereof of each of the mentioned embodiments is contemplated to be within the scope of the invention.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be understood by those of skill in the art that certain compounds of the present invention may exist in solvated, for example hydrated, as well as unsolvated forms. It will further be understood that the present invention encompasses all such solvated forms of the compounds of Formula I.

Within the scope of the invention are also salts of the compounds of Formula I. Generally, pharmaceutically acceptable salts of compounds of the present invention are obtained using standard procedures well known in the art.

In one embodiment of the present invention, the compound of Formula I may be converted to a pharmaceutically acceptable salt or solvate thereof, particularly, an acidic addition salt such as a hydrochloride, hydrobromide, phosphate, acetate, fumarate, maleate, tartrate, citrate, methanesulphonate or p-toluenesulphonate.

Process for Preparing

Compounds according to Formula I can be prepared by various synthetic processes as illustrated herein. The choice of particular structural features and/or substituents may therefore influence the selection of one process over another.

Within these general guidelines, processes described herein can be used to prepare exemplary subsets of compounds of this invention. Unless indicated otherwise, the variables in the described schemes and processes have the same definitions as those given for Formula I above.

A person of ordinary skill in the art thus will appreciate that variations and additions adapting one or more of the processes disclosed herein will permit synthesis of other compounds in accord with Formula I.

The invention is further illustrated by way of the following examples, which describe several embodiments of the invention. The synthetic scheme and the synthetic procedures provided for Examples 1, 2 and 4 are provided by way of illustration and are not to be construed as limiting the invention. It will be clear to those skilled in the art that other illustrated compounds may be readily prepared by processes analogous to those described.

Synthetic scheme:

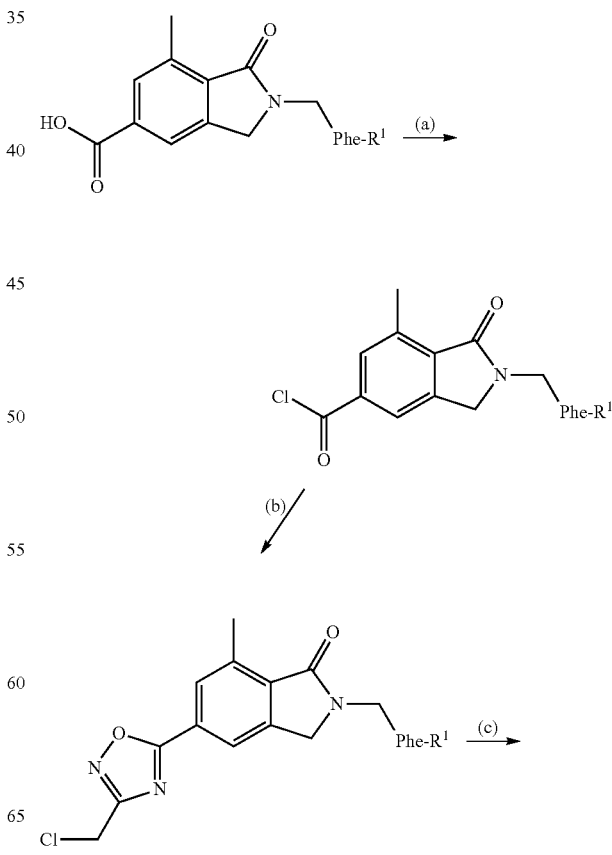

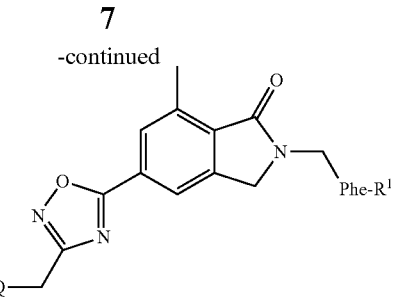

Reagents and conditions used in a typical procedure: (a) SOCl$_2$, Δ; (b) 2-chloro-N-hydroxyacetamidine, K$_2$CO$_3$, MeCN, then DMF, Δ; (c) QH, K$_2$CO$_3$, MeCN, Δ.

(a) In a typical procedure 100 mmol of a 7-methyl-1-oxo-2-(substituted-benzyl)-2,3-dihydro-1H-isoindole-5-carboxylic acid was dissolved in an excess of thionyl chloride and heated at reflux for 30 min. The reaction mixture was cooled to room temperature and concentrated to provide a 7-methyl-1-oxo-2-(substituted-benzyl)-2,3-dihydro-1H-isoindole-5-carbonyl chloride.

(b) To a solution of the 7-methyl-1-oxo-2-(substituted-benzyl)-2,3-dihydro-1H-isoindole-5-carbonyl chloride (100 mmol) in MeCN (50 mL) was added 2-chloro-N-hydroxyacetamidine (110 mmol) and K$_2$CO$_3$ (200 mmol). The mixture was stirred overnight, then diluted with water and extracted with EtOAc. The organic phase was washed with brine, dried (Na$_2$SO$_4$), filtered and concentrated. The residue was dissolved in DMF (50 mL) and heated at reflux for 3.5 h. The cooled solution was diluted with water and extracted with EtOAc. The organic phase was washed with brine, dried (Na$_2$SO$_4$), filtered and concentrated. Column chromatography on silica (10-35% EtOAc/hexanes) provided a 2-substituted-benzyl-5-(3-chloromethyl-[1,2,4]oxadiazol-5-yl)-7-methyl-2,3-dihydro-isoindol-1-one.

(c) To a solution of the 2-(substituted-benzyl)-5-(3-chloromethyl-[1,2,4]oxadiazol-5-yl)-7-methyl-2,3-dihydro-isoindol-1-one (100 mmol) in MeCN was added K$_2$CO$_3$ (200-300 mmol) and a suitable amine (QH, 150-200 mmol). The mixture was heated to provide a desired isoindolone that was purified by column chromatography on silica (1-5% 2M NH$_3$ in MeOH/CH$_2$Cl$_2$).

Example 1

7-Methyl-5-(3-piperazin-1-ylmethyl-[1,2,4]oxadiazol-5-yl)-2-(4-trifluoromethoxybenzyl)-2,3-dihydroisoindol-1-one

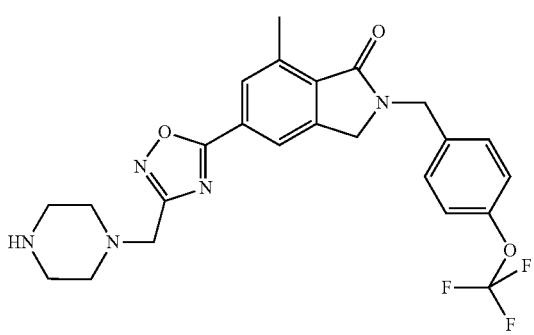 [SMILES: Cc1cc(-c2nc(CN3CCNCC3)no2)cc2c1C(=O)N(Cc1ccc(OC(F)(F)F)cc1)C2]

To a solution of 5-(3-chloromethyl-[1,2,4]-oxadiazol-5-yl)-7-methyl-2-(4-trifluoromethoxybenzyl)-2,3-dihydroisoindol-1-one (3.25 g, 7.43 mmol) in MeCN (50 mL) was added piperazine-1-carboxylic acid tert-butyl ester (2.77 g, 14.9 mmol) and K$_2$CO$_3$ (2.57 g, 18.6 mmol). The mixture was warmed to 40° C. for 24 h, then cooled to room temperature and diluted with water. The mixture was extracted with EtOAc and the organic phase was washed with brine, dried (Na$_2$SO$_4$), filtered, and concentrated. The residue was triturated with hexanes and filtered. Column chromatography on silica (40-80% EtOAc/hexanes) followed by trituration with 1% MeOH/Et$_2$O provided the Boc-protected intermediate (4.78 g) as a colourless solid.

The Boc-protected intermediate was dissolved in CH$_2$Cl$_2$ (15 mL) and 1:1 TFA/CH$_2$Cl$_2$ (40 mL) was added. After 45 min the reaction mixture was concentrated and basified with aqueous NaHCO$_3$ to pH ~9-10. The product was extracted with CH$_2$Cl$_2$. The organic phase was washed with brine, dried (Na$_2$SO$_4$), filtered, and concentrated. Column chromatography on silica (1-5% 2M NH$_3$ in MeOH/CH$_2$Cl$_2$) provided 7-methyl-5-(5-piperazin-1-ylmethyl-[1,2,4]oxadiazol-3-yl)-2-(4-trifluoromethoxybenzyl)-2,3-dihydroisoindol-1-one (3.79 g) as a colourless foam. $^1$H NMR (300 MHz, CDCl$_3$) δ 8.05 (s, 1H), 8.00 (s, 1H), 7.36 (d, 2H), 7.20 (d, 2H), 4.81 (s, 2H), 4.33 (s, 2H), 3.77 (s, 2H), 2.94-3.05 (m, 4H), 2.84 (s, 3H), 2.61 (br s, 4H).

Example 2

2-(4-Chloro-benzyl)-5-[3-(2,5-diaza-bicyclo[2.2.1]hept-2-ylmethyl)-[1,2,4]oxadiazol-5-yl]-7-methyl-2,3-dihydro-isoindol-1-one

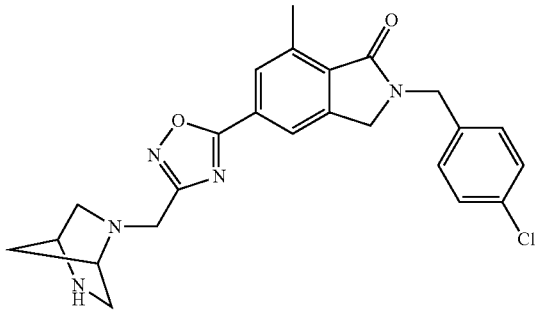 [SMILES: Cc1cc(-c2nc(CN3CC4CC3CN4)no2)cc2c1C(=O)N(Cc1ccc(Cl)cc1)C2]

To a solution of 2-(4-chloro-benzyl)-5-(3-chloromethyl-[1,2,4]oxadiazol-5-yl)-7-methyl-2,3-dihydroisoindol-1-one (40 mg, 0.103 mmol) in MeCN (4 mL) was added K$_2$CO$_3$ (0.309 mmol) and (1s, 4s)-2,5-diaza-bicyclo[2.2.1]heptane-2-carboxylic acid tert-butyl ester (31 mg, 0.154 mmol). The mixture was heated at 60° C. overnight. The reaction was cooled and diluted with water, then extracted with EtOAc. The organic phase was washed with brine, dried (Na$_2$SO$_4$), filtered and concentrated. Column chromatography on silica (1% 2M NH$_3$ in MeOH/CH$_2$Cl$_2$) provided 2-(4-chlorobenzyl)-5-[3-(2,5-diazabicyclo[2.2.1]hept-2-ylmethyl)-[1,2,4]oxadiazol-5-yl]-7-methyl-2,3-dihydroisoindol-1-one as a brown solid (27 mg). $^1$H NMR (300 MHz, CDCl$_3$) δ 8.04 (s, 1H), 7.99 (s, 1H), 7.37 (d, 2H), 7.26 (d, 2H), 4.77 (s, 2H), 4.30

(s, 2H), 3.94 (dd, 2H), 3.58 (d, 2H), 3.26 (d, 1H), 3.11 (d, 1H), 2.89 (d, 1H), 2.84 (s, 3H), 2.63 (d, 1H), 1.88 (d, 1H), 1.66 (d, 1H).

Example 4

2-(4-Chloro-benzyl)-7-methyl-5-(3-piperazin-1-ylmethyl-[1,2,4]oxadiazol-5-yl)-2,3-dihydro-isoindol-1-one

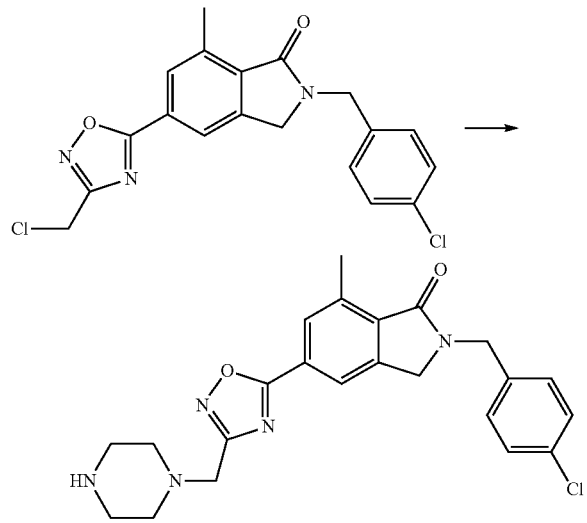

To a solution of 2-(4-chloro-benzyl)-5-(3-chloromethyl-[1,2,4]oxadiazol-5-yl)-7-methyl-2,3-dihydroisoindol-1-one (40 mg, 0.103 mmol) in MeCN (4 mL) was added $K_2CO_3$ (3.0 eq.) and piperazine-1-carboxylic acid tert-butyl ester (29 mg, 0.154 mmol). The mixture was heated at 70° C. for 1 week. The reaction was cooled and diluted with water, then extracted with EtOAc. The organic phase was washed with brine, dried ($Na_2SO_4$), filtered, and concentrated. Column chromatography on silica (10-50% EtOAc/hexanes) provided the Boc-protected intermediate as an oil. This residue was dissolved in 1:1 TFA/$CH_2Cl_2$ for 30 min, then the reaction mixture was concentrated and basified with aqueous $NaHCO_3$ to pH ~9-10. The product was extracted with $CH_2Cl_2$. The organic phase was washed with brine, dried ($Na_2SO_4$), filtered, and concentrated. The residue was dissolved in EtOAc and extracted with 1M HCl. The aqueous phases were basified with 6M NaOH and extracted with $CH_2Cl_2$. The organic phase was dried ($Na_2SO_4$), filtered, and concentrated to provide 2-(4-chlorobenzyl)-7-methyl-5-(3-piperazin-1-ylmethyl-[1,2,4]oxadiazol-5-yl)-2,3-dihydroisoindol-1-one as a colourless oil (29 mg). $^1$H NMR (300 MHz, $CDCl_3$) δ 8.05 (s, 1H), 7.99 (s, 1H), 7.34 (d, 2H), 7.26 (d, 2H), 4.77 (s, 2H), 4.31 (s, 2H), 3.77 (s, 2H), 2.97 (br s, 4H), 2.84 (s, 3H), 2.62 (br s, 4H).

Compounds shown in the following table illustrate the invention:

| Ex. No. | Structure | Name | $^1$H NMR |
|---|---|---|---|
| 1 | 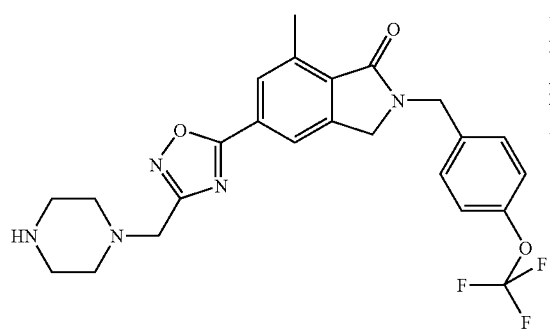 [SMILES: Cc1cc(-c2nc(CN3CCNCC3)no2)cc2c1C(=O)N(Cc1ccc(OC(F)(F)F)cc1)C2] | 7-Methyl-5-(3-piperazin-1-ylmethyl-[1,2,4]oxadiazol-5-yl)-2-(4-trifluoromethoxybenzyl)-2,3-dihydroisoindol-1-one | δ 8.05 (s, 1H), 8.00 (s, 1H), 7.36 (d, 2H), 7.20 (d, 2H), 4.81 (s, 2H), 4.33 (s, 2H), 3.77 (s, 2H), 2.94-3.05 (m, 4H), 2.84 (s, 3H), 2.61 (br s, 4H). |
| 2 | 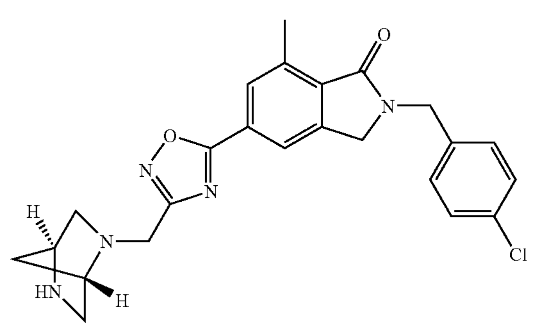 [SMILES: Cc1cc(-c2nc(CN3C[C@@H]4C[C@H]3CN4)no2)cc2c1C(=O)N(Cc1ccc(Cl)cc1)C2] | 2-(4-Chloro-benzyl)-5-[3-(2,5-diazabicyclo[2.2.1]hept-2-ylmethyl)-[1,2,4]oxadiazol-5-yl]-7-methyl-2,3-dihydro-isoindol-1-one | δ 8.04 (s, 1H), 7.99 (s, 1H), 7.26-7.35 (m, 4H), 4.83 (s, 2H), 4.00 (s, 2H), 3.94 (dd, 2H), 3.58 (d, 2H), 3.18 (d, 1H), 3.11 (dd, 1H), 2.89 (d, 1H), 2.78 (s, 3H), 2.64 (d, 1H), 1.64-1.92 (m, 6H). |

-continued

| Ex. No. | Structure | Name | $^1$H NMR |
|---|---|---|---|
| 3 | 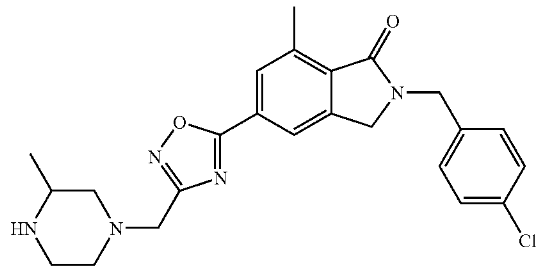 [SMILES: Cc1cc(-c2nc(CN3CCNC(C)C3)no2)cc2c1C(=O)N(Cc1ccc(Cl)cc1)C2] | 2-(4-Chloro-benzyl)-7-methyl-5-[3-(3-methyl-piperazin-1-ylmethyl)-[1,2,4]oxadiazol-5-yl]-2,3-dihydro-isoindol-1-one | δ 8.04 (s, 1H), 7.99 (s, 1H), 7.25-7.35 (m, 4H), 4.77 (s, 2H), 4.30 (s, 2H), 3.72 (s, 3H), 2.84-3.01 (m, 5H), 2.84 (s, 3H), 2.25 (ddd, 1H), 1.89 (t, 1H), 1.26 (dd, 1H), 1.04 (d, 3H). |
| 4 | 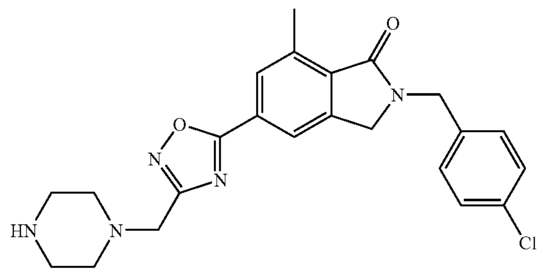 [SMILES: Cc1cc(-c2nc(CN3CCNCC3)no2)cc2c1C(=O)N(Cc1ccc(Cl)cc1)C2] | 2-(4-Chloro-benzyl)-7-methyl-5-(3-piperazin-1-ylmethyl-[1,2,4]oxadiazol-5-yl)-2,3-dihydro-isoindol-1-one | δ 8.05 (s, 1H), 7.99 (s, 1H), 7.26-7.35 (m, 4H), 4.77 (s, 2H), 4.31 (s, 2H), 3.77 (s, 2H), 2.97 (br s, 4H), 2.84 (s, 3H), 2.62 (br s, 4H). |
| 5 | 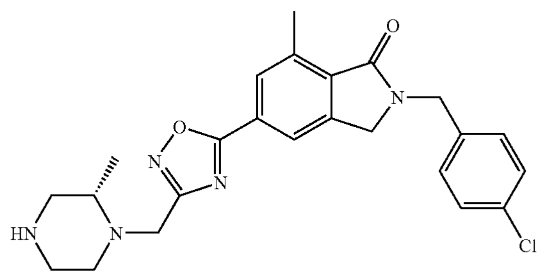 [SMILES: Cc1cc(-c2nc(CN3CCNC[C@@H]3C)no2)cc2c1C(=O)N(Cc1ccc(Cl)cc1)C2] | 2-(4-Chloro-benzyl)-7-methyl-5-[3-(2-methyl-piperazin-1-ylmethyl)-[1,2,4]oxadiazol-5-yl]-2,3-dihydro-isoindol-1-one | δ 8.02 (s, 1H), 7.97 (s, 1H), 7.26-7.35 (m, 4H), 4.81 (s, 2H), 4.31 (s, 2H), 3.98 (d, 2H), 2.85-2.96 (m, 4H), 2.85 (s, 3H), 2.51-2.64 (m, 3H), 1.22 (d, 3H). |
| 6 | 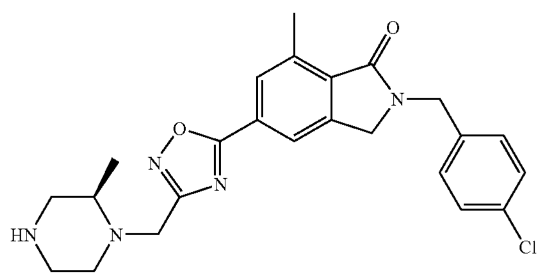 [SMILES: Cc1cc(-c2nc(CN3CCNC[C@H]3C)no2)cc2c1C(=O)N(Cc1ccc(Cl)cc1)C2] | 2-(4-Chloro-benzyl)-7-methyl-5-[3-(2-methyl-piperazin-1-ylmethyl)-[1,2,4]oxadiazol-5-yl]-2,3-dihydro-isoindol-1-one | δ 8.02 (s, 1H), 7.97 (s, 1H), 7.26-7.35 (m, 4H), 4.81 (s, 2H), 4.31 (s, 2H), 3.98 (d, 2H), 2.85-2.96 (m, 4H), 2.85 (s, 3H), 2.51-2.64 (m, 3H), 1.22 (d, 3H). |

Pharmaceutical Compositions

The compounds described herein may be generally formulated into a pharmaceutical composition comprising a compound of Formula I or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substance, which may also act as diluents, flavoring agents, solubilizers, lubricants, suspending agents, binders or table disintegrating agents. A solid carrier can also be an encapsulating material.

In powders, the carrier is a finely divided solid, which is in a mixture with the finely divided compound active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be made as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

Compounds described herein exhibit activity as modulators of metabotropic glutamate receptors and more particularly exhibit activity as potentiators of the mGluR2 receptor. It is contemplated that the compounds will be useful in therapy as pharmaceuticals, in particular for the treatment of neurological and psychiatric disorders associated with glutamate dysfunction in an animal and particularly in a human.

More specifically, the neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to Formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to Formula I or a pharmaceutically acceptable salt or solvate thereof, is administered to a patient in need of such treatment. The invention also provides a compound of Formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders.

In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracically, intravenously, epidurally, intrathecally, intracerebroventricularly and by injection into the joints. In preferred embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of Formula I, or salts thereof, are useful as pharmacological tools in the development and standardization of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

General Methods

Starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated.

All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadrapole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.).

Preparative reversed phase chromatography was run on a Gilson autopreparative HPLC with a diode array detector using an XTerra MS C8, 19×300 mm, 7 mm as column.

Purification by a Chromatotron was performed on rotating silica gel/gypsum (Merck, 60 PF-254 with calcium sulphate) coated glass sheets, with coating layer of 1, 2, or 4 mm using a TC Research 7924T Chromatotron.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

Microwave heating was performed in a Smith Synthesizer Single-mode microwave cavity producing continuous irradiation at 2450 MHz (Personal Chemistry AB, Uppsala, Sweden).

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al., 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

hERG activity was assessed using the process described by Bridgland-Taylor, M. H., et al, J. Pharm. Tox. Methods 54 (2006) 189-199.

Solubility was determined in pH 7.4 phosphate buffer after equilibration for 24 h at 25° C. and HPLC-UV and LC-MSMS were used for quantitation.

A $[^{35}S]$-GTPγS binding assay was used to functionally assay mGluR2 receptor activation. The allosteric activator activity of compounds at the human mGluR2 receptor were measured using a $[^{35}S]$-GTPγS binding assay with membranes prepared from CHO cells which stably express the human mGluR2. The assay is based upon the principle that agonists bind to G-protein coupled receptors to stimulate GDP-GTP exchange at the G-protein. Since $[^{35}S]$-GTPγS is a non-hydrolyzable GTP analog, it can be used to provide an index of GDP-GTP exchange and, thus, receptor activation. The GTPγS binding assay therefore provides a quantitative measure of receptor activation.

Membranes were prepared from CHO cells stably transfected with human mGluR2. Membranes (30 μg protein) were incubated with test compound (3 nM to 300 μM) for 15 minutes at room temperature prior to the addition of 1 μM glutamate, and incubated for 30 min at 30° C. in 500 μl assay buffer (20 mM HEPES, 100 mM NaCl, 10 mM $MgCl_2$), containing 30 μM GDP and 0.1 nM $[^{35}S]$-GTPγS (1250 Ci/mmol). Reactions were carried out in triplicate in 2 ml polypropylene 96-well plates. Reactions were terminated by vacuum filtration using a Packard 96-well harvester and Unifilter-96, GF/B filter microplates. The filter plates were washed 4×1.5 ml with ice-cold wash buffer (10 mM sodium phosphate buffer, pH 7.4). The filter plates were dried and 35 μl of scintillation fluid (Microscint 20) was added to each well. The amount of radioactivity bound was determined by counting plates on the Packard TopCount. Data was analyzed using GraphPad Prism, and $EC_{50}$ and $E_{max}$ values (relative to the maximum glutamate effect) were calculated using non-linear regression.

As illustrated in the Table below, generally, compounds described herein have favourable solubility, low capacity to activate the hERG ion channel and were highly active in assays described herein for mGluR2 modulator activity, having $EC_{50}$ values as shown.

TABLE

| Example No. | GTPgS $EC_{50}$ μM | Aqueous solubility μM | hERG μM |
|---|---|---|---|
| 1 | 0.231 | 44.9 | 11.0 |
| 2 | 0.206 | 336.5 | 33.0 |
| 3 | 0.154 | 396.1 | 12.0 |
| 4 | 0.378 | >500 | 25.0 |
| 5 | 0.352 | 383.9 | 12.6 |
| 6 | 0.317 | >500 | 18.7 |

What is claimed is:

1. A compound that is: 7-methyl-5-(3-piperazin-1-ylm-ethyl-[1,2,4]oxadiazol-5-yl)-2-(4-trifluoromethoxybenzyl)-2,3-dihydroisoindol-1-one having the following structure;

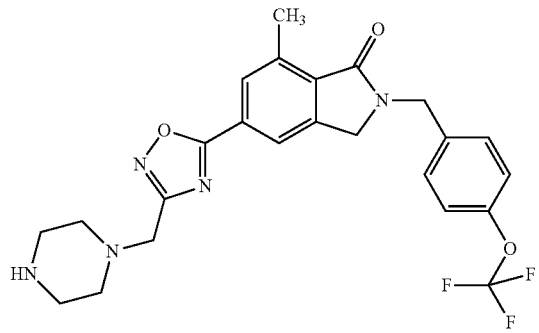 [SMILES: Cc1cc(-c2nc(CN3CCNCC3)no2)cc2c1C(=O)N(Cc1ccc(OC(F)(F)F)cc1)C2]

or a pharmaceutically acceptable salt thereof, a hydrate thereof, or a combination of said compound, salt or hydrate.

2. A pharmaceutical composition comprising a compound or a pharmaceutically acceptable salt or a hydrate or a combination according to claim 1 and a pharmaceutically acceptable carrier or excipient.

3. A method for the treatment schizophrenia, anxiety, or generalized anxiety disorder in an animal in need of such treatment, comprising the step of administering to said animal a therapeutically effective amount of a compound or a pharmaceutically acceptable salt or a hydrate or a combination according to claim 1.

4. A method for the treatment schizophrenia, anxiety, or generalized anxiety disorder in an animal in need of such treatment, comprising the step of administering to said animal a therapeutically effective amount of a pharmaceutical composition according to claim 2.

* * * * *